United States Patent
Kwak et al.

(10) Patent No.: US 11,169,130 B2
(45) Date of Patent: Nov. 9, 2021

(54) ELECTRONIC DEVICE INCLUDING REPLACEABLE SENSOR

(71) Applicant: Samsung Electronics Co., Ltd., Gyeonggi-do (KR)

(72) Inventors: Dong Uk Kwak, Gyeonggi-do (KR); Min Ho Park, Gyeonggi-do (KR); Hyun Cheol Park, Daegu (KR); Sung Gun Bae, Gyeonggi-do (KR); Ik Joo Byun, Gyeonggi-do (KR); Seung Goo Lee, Gyeonggi-do (KR); Dae Ung Jeong, Gyeonggi-do (KR); Jeong Min Park, Gyeonggi-do (KR)

(73) Assignee: Samsung Electronics Co., Ltd.

( * ) Notice: Subject to any disclaimer, the term of this patent is extended or adjusted under 35 U.S.C. 154(b) by 536 days.

(21) Appl. No.: 16/170,520

(22) Filed: Oct. 25, 2018

(65) Prior Publication Data

US 2019/0120805 A1 Apr. 25, 2019

(30) Foreign Application Priority Data

Oct. 25, 2017 (KR) .......................... 10-2017-0139447

(51) Int. Cl.
*G01N 33/00* (2006.01)
*G01N 1/22* (2006.01)
(Continued)

(52) U.S. Cl.
CPC ....... *G01N 33/0027* (2013.01); *G01D 11/245* (2013.01); *G01N 1/2205* (2013.01);
(Continued)

(58) Field of Classification Search
CPC .. G01D 11/24; G01D 11/245; G01N 33/0009; G01N 33/0027; G01N 33/0037;
(Continued)

(56) References Cited

U.S. PATENT DOCUMENTS 9,396,427 B2   7/2016 Cho
9,706,676 B2 *  7/2017 Moon ..................... H01Q 1/12
(Continued)

FOREIGN PATENT DOCUMENTS

DE        10159436     6/2003
JP       2010025728    2/2010
(Continued)

OTHER PUBLICATIONS

Database WPI Week 200830 Thomson Scientific, AN 2008-E40911, XP002790303, Mar. 9, 2007, 2 pages.
(Continued)

*Primary Examiner* — Nathaniel J Kolb
(74) *Attorney, Agent, or Firm* — The Farrell Law Firm, P.C.

(57) ABSTRACT

An electronic device is provided. The electronic device includes a display disposed toward a first surface, a housing including an opening formed toward a second surface, a tray including a hole formed toward the second surface, a sensor module that is able to be seated on the tray, a connector disposed adjacent to the opening inside the electronic device to receive the tray and the sensor module, and a processor configured to control the sensor module when the sensor module is inserted into the connector. The sensor module includes a gas sensor, a sensor chamber, and a pipe forming a path allowing gas, which is introduced through the hole, to move into the sensor chamber.

19 Claims, 12 Drawing Sheets

(51) Int. Cl.
  *H04M 1/02* (2006.01)
  *G06F 1/16* (2006.01)
  *G01D 11/24* (2006.01)

(52) U.S. Cl.
  CPC ....... *G01N 1/2273* (2013.01); *G01N 33/0009* (2013.01); *G06F 1/1656* (2013.01); *G06F 1/1658* (2013.01); *H04M 1/026* (2013.01); *G01N 33/004* (2013.01); *G01N 33/0037* (2013.01); *G01N 33/0044* (2013.01); *G01N 33/0047* (2013.01); *G01N 2001/2276* (2013.01); *H04M 2250/12* (2013.01)

(58) Field of Classification Search
  CPC ............. G01N 33/004; G01N 33/0044; G01N 33/0047; G01N 1/2205; G01N 1/2273; G01N 2001/2276; H04M 1/026; H04M 2250/12; G06F 1/1656; G06F 1/1658
  See application file for complete search history.

(56) References Cited

U.S. PATENT DOCUMENTS

| | | | |
|---|---|---|---|
| 9,766,092 B2 | 9/2017 | Chung et al. | |
| 9,859,936 B2* | 1/2018 | Lee | H04M 1/026 |
| 9,999,149 B2 | 6/2018 | Jun et al. | |
| 10,135,960 B2* | 11/2018 | Han | G08B 21/14 |
| 10,310,562 B2* | 6/2019 | Choi | G06F 1/1658 |
| 10,393,544 B2 | 8/2019 | Chung et al. | |
| 2014/0193018 A1* | 7/2014 | Lim | H04R 1/028 |
| | | | 381/334 |
| 2014/0374491 A1 | 12/2014 | Cho | |
| 2015/0132855 A1* | 5/2015 | Martin | G06F 13/385 |
| | | | 436/20 |
| 2015/0334859 A1* | 11/2015 | Lee | H05K 5/0217 |
| | | | 361/749 |
| 2016/0113142 A1* | 4/2016 | Moon | H04B 1/3818 |
| | | | 361/807 |
| 2016/0124498 A1 | 5/2016 | Chung et al. | |
| 2016/0164204 A1* | 6/2016 | Cho | G06K 19/07739 |
| | | | 439/152 |
| 2016/0360632 A1* | 12/2016 | Lee | H04B 1/3818 |
| 2017/0046938 A1 | 2/2017 | Hummer | |
| 2017/0108897 A1* | 4/2017 | Choi | G06F 1/1658 |
| 2017/0214423 A1* | 7/2017 | Park | G06K 7/0073 |
| 2017/0251564 A1 | 8/2017 | Jun et al. | |
| 2018/0003520 A1 | 1/2018 | Chung et al. | |
| 2018/0109658 A1* | 4/2018 | Le | H04M 1/03 |
| 2018/0110148 A9 | 4/2018 | Jun et al. | |
| 2018/0182223 A1 | 6/2018 | Hummer | |
| 2020/0366782 A1* | 11/2020 | Liao | G01N 33/0027 |

FOREIGN PATENT DOCUMENTS

| | | |
|---|---|---|
| KR | 100690638 | 2/2007 |
| KR | 101264562 | 5/2013 |
| KR | 1020160052153 | 5/2016 |
| KR | 1020160084410 | 7/2016 |
| KR | 1020170082941 | 7/2017 |
| KR | 1020170100368 | 9/2017 |
| WO | WO 2015/065390 | 5/2015 |

OTHER PUBLICATIONS

European Search Report dated Apr. 25, 2019 issued in counterpart application No. 18202609.6-1001, 7 pages.
Korean Office Action dated Sep. 27, 2021 issued in counterpart application No. 10-2017-0139447, 13 pages.

* cited by examiner

ELECTRONIC DEVICE INCLUDING REPLACEABLE SENSOR

CROSS-REFERENCE TO RELATED APPLICATION(S)

This application is based on and claims priority under 35 U.S.C. § 119 to Korean Patent Application Serial No. 10-2017-0139447, filed on Oct. 25, 2017, in the Korean Intellectual Property Office, the entire disclosure of which is incorporated herein by reference.

BACKGROUND

1. Field

The present disclosure relates generally to an electronic device including a replaceable sensor.

2. Description of Related Art

Electronic devices, such as smart phones, tablet personal computers (PCs) or the like, may perform various functions such as conversations, moving picture reproduction, and the searching for the Internet. In addition, the electronic device may recognize the motion of a user and may collect various pieces of information (e.g., brightness, sound, or the like) on surroundings by using various sensors.

Recently, an electronic device has been launched with a gas sensor. The gas sensor may analyze a component of gas included in the air and may convert the analysis result into an electrical signal. The gas sensor may be employed in various fields such as the recognition of bad breath or the detection of toxic gas.

An electrochemical gas sensor mounted on an electronic device according to the related art analyzes the component of gas by using an electrolyte. In the case of the electronic device having the electrochemical gas sensor, when the electrolyte is consumed and thus the performance of the electrochemical gas sensor is degraded, the electrochemical gas sensor may not be replaced with a new one. In the case of an electronic device having a semiconductor-type gas sensor that is unable to be replaced, when the performance of the semiconductor-type gas sensor is degraded, the component of the gas may not be exactly measured.

SUMMARY

The present disclosure has been made to address at least the disadvantages described above and to provide at least the advantages described below.

In accordance with an aspect of the present disclosure, an electronic device is provided. The electronic device includes a display disposed toward a first surface, a housing including an opening formed toward a second surface, a tray including a hole formed toward the second surface, a sensor module that is able to be seated on the tray, a connector disposed adjacent to the opening inside the electronic device to receive the tray and the sensor module, and a processor configured to control the sensor module when the sensor module is inserted into the connector. The sensor module includes a gas sensor, a sensor chamber, and a pipe forming a path allowing gas, which is introduced through the hole, to move into the sensor chamber.

BRIEF DESCRIPTION OF THE DRAWINGS

The above and other aspects, features and advantages of certain embodiments of the disclosure will be more apparent from the following detailed description taken in conjunction with the accompanying drawings, in which.

DETAILED DESCRIPTION

Figure 1:
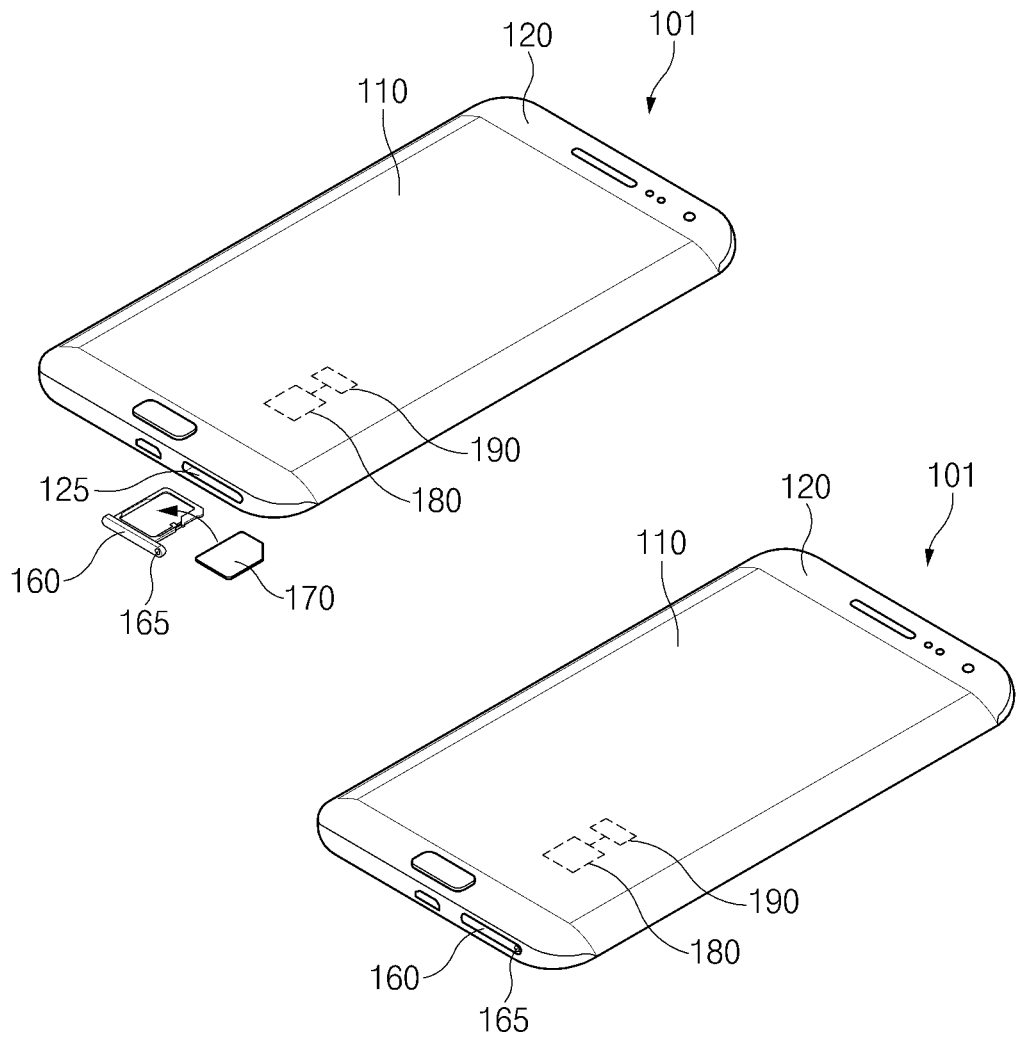
FIG. 1 is a diagram of an electronic device including a replaceable sensor module, according to an embodiment.

Hereinafter, various embodiments of the present disclosure will be described with reference to the accompanying drawings. Accordingly, those of ordinary skill in the art will recognize that modification, equivalent, and/or alternative on the various embodiments described herein can be variously made without departing from the scope and spirit of the present disclosure. With regard to description of drawings, similar components may be marked by similar reference numerals.

In the disclosure disclosed herein, the expressions "have", "may have", "include" and "comprise", or "may include" and "may comprise" used herein indicate existence of corresponding features (for example, elements such as numeric values, functions, operations, or components) but do not exclude presence of additional features.

In the disclosure disclosed herein, the expressions "A or B", "at least one of A or/and B", or "one or more of A or/and B", and the like used herein may include any and all combinations of one or more of the associated listed items. For example, the term "A or B", "at least one of A and B", or "at least one of A or B" may refer to all of the case (1) where at least one A is included, the case (2) where at least one B is included, or the case (3) where both of at least one A and at least one B are included.

The terms, such as "first", "second", and the like used herein may refer to various elements of various embodiments of the present disclosure, but do not limit the elements. For example, such terms are used only to distinguish an element from another element and do not limit the order and/or priority of the elements. For example, a first user device and a second user device may represent different user devices irrespective of sequence or importance. For example, without departing the scope of the present disclosure, a first element may be referred to as a second element, and similarly, a second element may be referred to as a first element.

It will be understood that when an element (for example, a first element) is referred to as being "(operatively or communicatively) coupled with/to" or "connected to" another element (for example, a second element), it can be directly coupled with/to or connected to the other element or an intervening element (for example, a third element) may be present. In contrast, when an element (for example, a first element) is referred to as being "directly coupled with/to" or "directly connected to" another element (for example, a second element), it should be understood that there are no intervening element (for example, a third element).

According to the situation, the expression "configured to" used herein may be used as, for example, the expression "suitable for", "having the capacity to", "designed to", "adapted to", "made to", or "capable of". The term "configured to (or set to)" must not mean only "specifically designed to" in hardware. Instead, the expression "a device configured to" may mean that the device is "capable of" operating together with another device or other components. For example, a "processor configured to (or set to) perform A, B, and C" may mean a dedicated processor (for example, an embedded processor) for performing a corresponding operation or a generic-purpose processor (for example, a central processing unit (CPU) or an application processor) which may perform corresponding operations by executing one or more software programs which are stored in a memory device.

Terms used in this specification are used to describe specified embodiments of the present disclosure and are not intended to limit the scope of the present disclosure. The terms of a singular form may include plural forms unless otherwise specified. Unless otherwise defined herein, all the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal meaning unless expressly so defined herein in various embodiments of the present disclosure. In some cases, even if terms are terms which are defined in the specification, they may not be interpreted to exclude embodiments of the present disclosure.

An electronic device according to various embodiments of the present disclosure may include at least one of smartphones, tablet personal computers (PCs), mobile phones, video telephones, electronic book readers, desktop PCs, laptop PCs, netbook computers, workstations, servers, personal digital assistants (PDAs), portable multimedia players (PMPs), MP3 players, mobile medical devices, cameras, and wearable devices. According to various embodiments of the present disclosure, the wearable devices may include accessories (for example, watches, rings, bracelets, ankle bracelets, glasses, contact lenses, or head-mounted devices (HMDs)), cloth-integrated types (for example, electronic clothes), body-attached types (for example, skin pads or tattoos), or implantable types (for example, implantable circuits).

Hereinafter, electronic devices according to an embodiment of the present disclosure will be described with reference to the accompanying drawings. The term "user" used herein may refer to a person who uses an electronic device or may refer to a device (for example, an artificial intelligence electronic device) that uses an electronic device.

FIG. 1 is a diagram of an electronic device including a replaceable sensor module, according to an embodiment.

Referring to FIG. 1, an electronic device 101 includes a display 110, a housing (or a body) 120, a tray 160, a sensor module 170, a processor 180, and a memory 190.

The display 110 may output content such as a text or an image. The display 110 may output a user interface of an application for managing the health state of a user. The display 110 may display a user interface based on information recognized through the sensor module 170 (e.g. a card-type sensor for analyzing gas). The display 110 may display a measurement result based on information on bad breath of the user measured through the sensor module 170.

The housing (or the body part) 120 may fix the display 110 and may protect various components inside the housing 120. The housing 120 may include a button, a sensor window, or a speaker disposed outside the housing 120.

The housing 120 may include an opening 125 for inserting the sensor module 170 into the electronic device 101. The tray 160 having the sensor module 170 seated thereon may be inserted into the electronic device 101 through the opening 125.

The electronic device 101 may include a connector (not illustrated) provided adjacent to the opening 125 and used to mount the tray 160. The connector may include various components such as a sensor reader part (or a contact area) that may be electrically connected with the sensor module 170 and a structure for withdrawing the tray 160 to the outside. The additional information on the connector is provided with respect to FIGS. 2, 6, and 7.

The tray 160 may be used to mount (seat) the sensor module 170. The tray 160 may have a shape corresponding to the shape of the sensor module 170. The tray 160 may include a hole 165. When a pin is inserted through the hole 165 and external pressure is applied to the pin, the tray 160 may be withdrawn out of the electronic device 101.

The hole 165 may serve as a passage for introducing air into the gas sensor mounted in the sensor module 170. The sensor module 170 may analyze the air introduced through the hole 165 and may generate an electrical signal.

The tray 160 may be implemented in the shape the same as or compatible with the shape of a tray for mounting a general USIM or micro-SD card.

Although FIG. 1 illustrates that the tray 160 having the sensor module 170 mounted thereon is inserted through a lower portion of a side surface of the electronic device 101, the present disclosure is not limited thereto. For example, the tray 160 may be inserted through an upper side surface or a left/right side surface of the electronic device 101.

Although FIG. 1 illustrates that one sensor module 170 is seated on the tray 160, the present disclosure is not limited thereto. For example, the tray 160 may have two card regions. The card regions may be seated therein with a plurality of sensor modules, which are different from each other, or with one sensor module and one SIM card. Additional information on the tray for seating a plurality of cards is described with reference to FIG. 8.

The sensor module 170 (or a sensor unit, a sensor device, or a card-type sensor; for example, a gas recognizing sensor) may be seated on the tray 160 and inserted into the electronic device 101. The sensor module 170 may have the shape the same as or compatible with the shape of the outer appearance of a general USIM card or micro-SD card, or the like.

The sensor module 170 may chemically analyze various gas components of the air through the gas sensor provided therein. The sensor module 170 may include a chemical sensor for analyzing various types of gas, such as total volatile organic compounds (TVOC), carbon monoxide (CO), carbon dioxide ($CO_2$), formaldehyde ($CH_2O$), or ethanol ($C_2H_5OH$). The user may use various types of sensor modules 170 depending on a use environment or a gas measuring environment through replacement.

The sensor module 170 may chemically analyze components of air introduced through the hole 165. The sensor module 170 may analyze air introduced through a pipe spatially connected with the hole 165 and may convert the analysis result into an electrical signal.

The sensor module 170 may include a sensor chamber having the shape surrounding the gas sensor. The sensor chamber may provide the air introduced through the hole 165 to the gas sensor and may block gas produced inside the electronic device 101. The additional information on the sensor module 170 is described with reference to FIGS. 3 to 7.

The housing (or the body part) 120 may include various components such as the processor 180, the memory 190, a communication circuit, a printed circuit board, a battery, or the like, which are necessary for driving the electronic device 101.

The processor 180 may display, on the display 110, the analysis result based on the electrical signal collected by the sensor module 170. The processor 180 may display, on the display 110, information on a chemical compositional ratio of the air introduced through the hole 165. The processor 180 may analyze breath introduced through the hole 165 and may display information on the level of bad breathe on the display 110.

Figure 2:
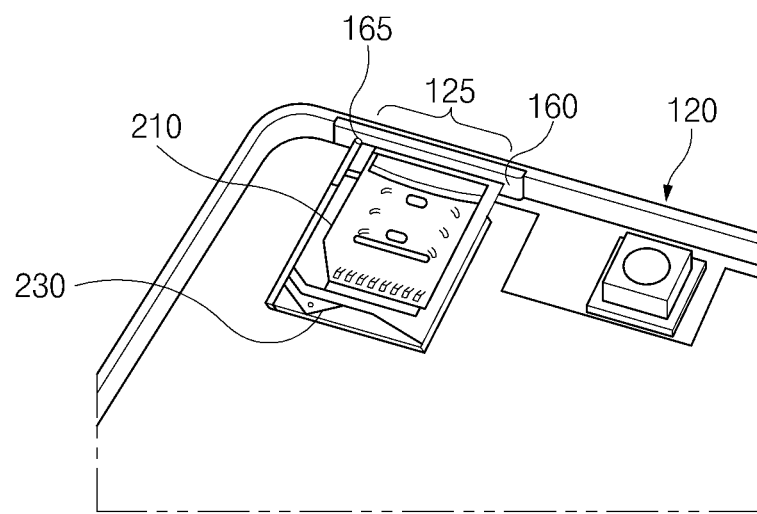
FIG. 2 is a diagram of a connector into which a tray is inserted, according to an embodiment.

FIG. 2 is a diagram of a connector into which the tray is inserted, according to an embodiment.

Referring to FIG. 2, the electronic device 101 includes a connector 210 formed in a region adjacent to the opening formed in the side surface of the electronic device 101. The connector 210 may receive the tray 160. The entrance of the connector 210 (a part into which the tray 160 is inserted) may be disposed close to the opening into which the tray 160 is inserted.

The connector 210 may include a sensor reader part (a contact region). The connector 210 may be electrically connected with the sensor module 170 seated on the tray 160 through the sensor reader part. The sensor reader part may include a power pin, a grounding pin, or a data pin, or the like. The additional information on the sensor reader part is described with reference to FIGS. 6 and 9.

The connector 210 may include a withdrawing structure 230. The withdrawing structure 230 may push the tray 160 out of the electronic device 101 by force applied from the outside. The withdrawing structure 230 may include a pressure part pressed by a pin inserted through the hole 165 of the tray 160 and may push the tray 160 out of the electronic device 101 through an operating part and a rotational shaft. The additional information on the withdrawing structure 230 is described with reference to FIG. 7.

The connector 210 may be spatially connected with the hole 165 and include a first passage extending in a direction that the tray 160 is inserted and a second passage for guiding air into the sensor chamber (or the chamber) of the sensor module. The second passage may maintain a specified angle (e.g., 90 degrees) with respect to the first passage. Additional information on the first passage and the second passage is described with reference to FIG. 7.

Figure 3:
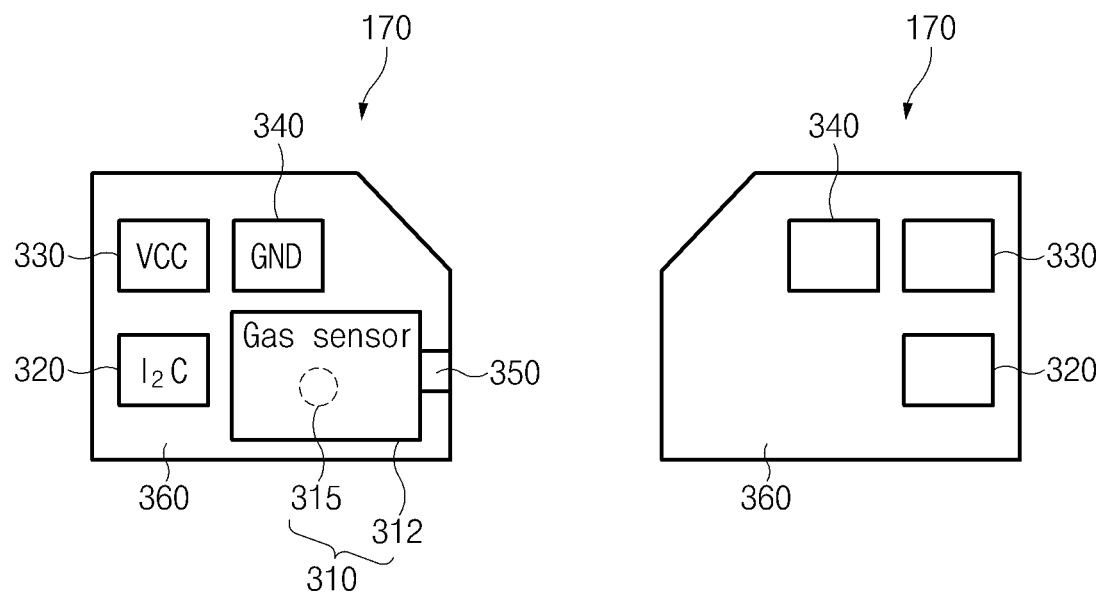
FIG. 3 is a diagram of a sensor module, according to an embodiment.

FIG. 3 is a diagram of a sensor module, according to an embodiment.

Referring to FIG. 3, the sensor module 170 includes a gas sensor unit 310, a data terminal 320, a power terminal 330, a grounding terminal 340, a pipe 350, and a substrate 360.

The gas sensor unit 310 may analyze the chemical component of the air introduced through the pipe 350. The gas sensor unit 310 includes a sensor chamber 312 and a gas sensor 315. The sensor chamber 312 may have the shape surrounding the gas sensor 315. The sensor chamber 312 may have a cavity formed around the gas sensor 315 to receive air introduced through the pipe 350. The sensor chamber 312 may provide the air, which is introduced through the hole 165 of FIG. 1, to the gas sensor 315 and may block gas, which is produced inside the electronic device 101 of FIG. 1, from being introduced into the gas sensor 315. The sensor chamber 312 may be formed by molding the gas sensor 315.

The data terminal 320 may perform data communication between the gas sensor 315 and the processor 180 inside the electronic device 101 as illustrated in FIG. 1. The data terminal 320 may transmit information on gas measurement, which is collected by the gas sensor 315, to the processor 180. The data terminal 320 may provide a control signal, which is received from the processor 180, to the gas sensor 315. The data terminal 320 may be a terminal making inter-integrated communication (I2C).

The power terminal 330 may transmit a power signal to operate the gas sensor 315.

The grounding terminal 340 may be connected with the grounding of the electronic device 101.

The pipe 350 may deliver the air, which is introduced through the hole 165 in FIG. 1, to the gas sensor unit 310. The pipe 350 may be spatially connected with the hole 165 formed in the tray 160 in FIG. 1. A tunnel may be formed between the hole 165 and the pipe 350 such that gas moves through the tunnel. The gas introduced through the hole 165 may move to the cavity around the gas sensor 315 through the tunnel and the pipe 350.

The substrate (e.g., the printed circuit board) 360 may fix the gas sensor unit 310, the data terminal 320, the power terminal 330, the grounding terminal 340, and the pipe 350. The substrate 360 may electrically connect the gas sensor 315, the data terminal 320, the power terminal 330, and the grounding terminal 340 with each other.

The data terminal 320, the power terminal 330, the grounding terminal 340 may be exposed to the back surface of the sensor module 170. The data terminal 320, the power terminal 330, the grounding terminal 340 may be electrically connected with pins of the connector 210 on the back surface of the substrate 360.

Figure 4:
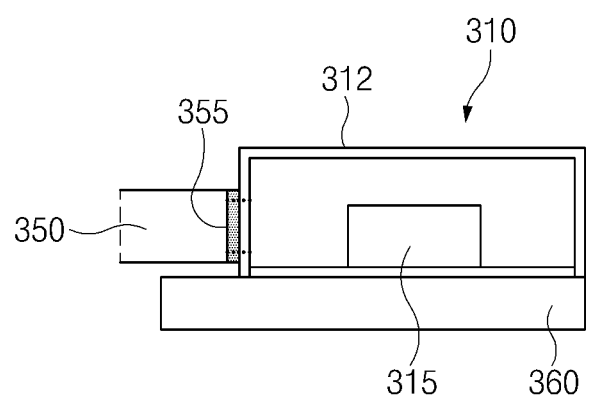
FIG. 4 is a diagram of a gas sensor unit and a pipe, according to an embodiment.

FIG. 4 is a diagram of a gas sensor unit and a pipe, according to an embodiment.

Referring to FIG. 4, the gas sensor unit 310 includes the sensor chamber 312 and the gas sensor 315. The sensor chamber 312 may have the shape surrounding the gas sensor 315. The sensor chamber 312 may have a cavity for receiving air introduced through the pipe 350. The sensor chamber 312 may provide the air, which is introduced through the pipe 350, to the gas sensor 315 and may block gas, which is produced from surrounding parts, from being introduced into the gas sensor 315. The sensor chamber 312 and the gas sensor 315 may be fixed to the substrate 360. The gas sensor 315 may be electrically connected with surrounding terminals or the internal circuit of the electronic device through the substrate 360.

The pipe 350 may be connected with the sensor chamber 312. The pipe 350 may provide the air, which is introduced through the hole of the tray, to the gas sensor 315 inside the sensor chamber 312. A membrane 355 may be interposed between the pipe 350 and the sensor chamber 312. The membrane 355 may block foreign matters such as moisture or dust, which may be introduced through the pipe 350, from being introduced into the sensor chamber 312. The membrane 355 may have a net structure, may pass gas, and may block a solid substance or a liquid from being introduced into the sensor chamber 312.

The gas sensor 315 may include a chemical specimen. The gas sensor 315 may convert the components of gas detected through the chemical specimen into an electrical signal. The gas sensor 315 may include chemical specimens such as CO, $C_2H_5OH$ or $CH_2O$. The gas sensor 315 may operate in a galvanic cell manner or in a potentiostatic electrolysis manner. The gas sensor 315 employing the galvanic cell manner may sense gas such as oxygen. The gas sensor employing the potentiostatic electrolysis manner may sense noxious gas (CO, NO, $H_2S$, or the like). When the gas sensor 315 specified to gas to be detected is mounted, the performance of detecting the gas may be enhanced.

When the gas sensor 315 operates in a manner of detecting gas by using the chemical specimen, the gas sensor 315 may be driven under lower power and may be manufactured in smaller size. In this case, the gas sensor 315 may have a disposable characteristic and may need to be periodically replaced with a new one. A user may maintain the performance of detecting gas by periodically replacing a sensor module including the gas sensor 315.

Figure 5:
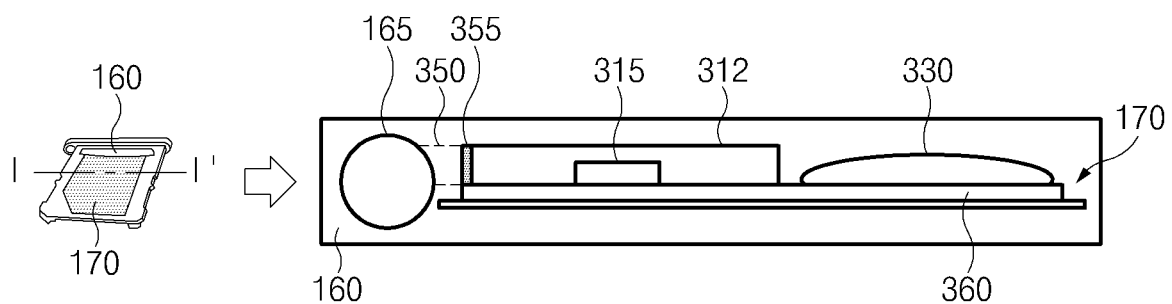
FIG. 5 is a diagram of a tray and a sensor module, according to an embodiment.

FIG. 5 is a diagram of a tray and a sensor module, according to an embodiment.

Referring to FIG. 5, the tray 160 may be used to mount (seat) the sensor module 170. The tray 160 may have a shape corresponding to the shape of the sensor module 170. The tray 160 may include the hole 165.

The hole 165 may serve as a passage for introducing air into the gas sensor 315 mounted in the sensor module 170. The air passing through the hole 165 may be introduced into the internal space of the sensor chamber 312 through the pipe 350 connected with the hole 165.

The membrane 355 may be interposed between the pipe 350 and the sensor chamber 312. The membrane 355 may block foreign matters such as moisture or dust, which may be introduced through the pipe 350, from being introduced into the sensor chamber 312. The membrane 355 may be disposed perpendicularly to the direction that the air is introduced.

The sensor chamber 312 may block the gas produced inside the electronic device 101 from being delivered to the gas sensor 315. The sensor chamber 312 may protect the gas sensor 315 from an external impact (e.g., a physical impact) or a foreign matter (e.g., water or dust).

The chemical specimen contained in the gas sensor 315 may be changed due to the gas introduced into the internal space of the sensor chamber 312 through the pipe 350. The gas sensor 315 may convert the result of the chemical change into an electrical signal.

The gas sensor 315 may maintain a specified distance from the pipe 350 (or the membrane 355). The distance is used to prevent the gas sensor 315 from being affected by other materials (e.g., moisture or dust) introduced into the pipe 350 (or the membrane 355).

The data terminal 320 may transmit the measurement result of the gas sensor 315 to the processor 180 inside the electronic device 101. For example, the data terminal 320 may be a terminal to support I2C communication. The data terminal 320 may make contact with a pin (e.g., a pogo pin) of a connector in which the tray is mounted.

Figure 6:
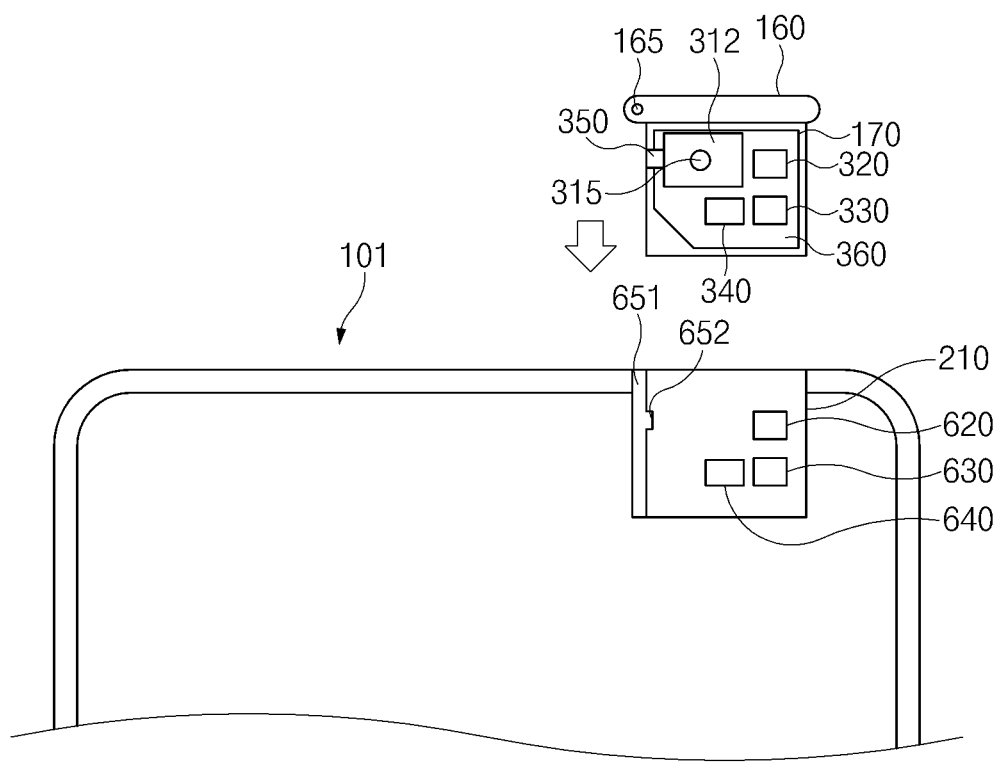
FIG. 6 is a diagram of a sensor reader part of the connector, according to an embodiment.

FIG. 6 is a diagram of a sensor reader part of the connector, according to an embodiment.

Referring to FIG. 6, the tray 160 may be used to mount (seat) the sensor module 170. The tray 160 may have the shape corresponding to the shape of the sensor module 170. The tray 160 may include the hole 165.

The sensor module 170 may be seated on the tray 160 and may be inserted into the electronic device 101. The sensor module 170 may include the sensor chamber 312, the gas sensor 315, the data terminal 320, the power terminal 330, the grounding terminal 340, the pipe 350, and the substrate 360.

The connector 210 may include a data pin 620, a power pin 630, and a grounding pin 640 corresponding to the data terminal 320, the power terminal 330, and the grounding terminal 340, respectively.

When the sensor module 170 is inserted into the connector 210, the data terminal 320, the power terminal 330, and the grounding terminal 340 may make contact with the data pin 620, the power pin 630, and the grounding pin 640, respectively.

The data pin 620 may be electrically connected with an internal processor of the electronic device 101. The data pin 620 may be a pin for making I2C communication.

The power pin 630 may be electrically connected with an internal power managing module (e.g., a battery) of the electronic device 101. The grounding pin 640 may be grounded inside the electronic device 101.

The connector 210 may include a first passage 651 and a second passage 652 used to pass the air introduced through the hole 165.

The first passage 651 may extend from the hole 165 in the direction that the tray 160 is inserted into the electronic device 101. The second passage 652 may connect the first passage 651 with the pipe 350 of the sensor module 170. When the sensor module 170 is inserted into the connector 210, the first passage 651, the second passage 652, and the pipe 350 are spatially connected with each other to form one passage allowing air to flow. The first passage 651 and the second passage 652 may be disposed perpendicular to each other.

The air introduced through the hole 165 may be provided to the gas sensor 315 through the first passage 651, the second passage 652, and the pipe 350.

Figure 7:
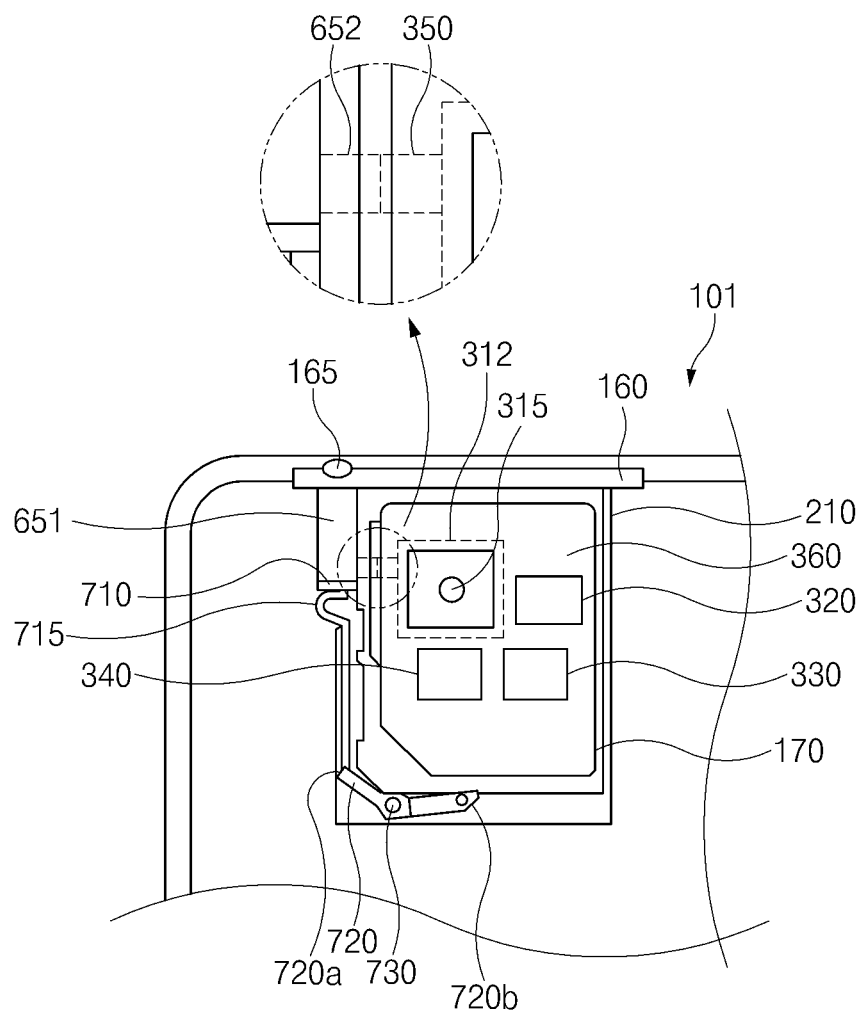
FIG. 7 is a diagram of the assembly of the sensor module and the connector, according to an embodiment.

FIG. 7 is a diagram of the assembly of the sensor module and the connector, according to an embodiment.

Referring to FIG. 7, the sensor module 170 may be seated on the tray 160 and may be inserted into the electronic device 101. The sensor module 170 may include the sensor chamber 312, the gas sensor 315, the data terminal 320, the power terminal 330, the grounding terminal 340, the pipe 350, and the substrate 360.

The connector 210 may include the data pin, the power pin, and the grounding pin. When the sensor module 170 is inserted into the connector 210, the data terminal 320, the power terminal 330, and the grounding terminal 340 may make contact with and electrically connected with the data pin 620, the power pin 630, and the grounding pin 640, respectively.

The connector 210 may include the first passage 651 and the second passage 652 used to pass through the air introduced through the hole 165.

The first passage 651 may extend from the hole 165 in the direction that the tray 160 is inserted into the electronic device 101. The second passage 652 may connect the first passage 651 with the pipe 350 of the sensor module 170. When the sensor module 170 is inserted into the connector 210, the first passage 651, the second passage 652, and the pipe 350 are spatially connected with each other to form one passage allowing air to flow. The first passage 651 and the second passage 652 may be disposed perpendicular to each other.

The connector 210 may include a withdrawing structure to withdraw the tray 160 out of the electronic device 101. The withdrawing structure may include a pressing unit 715, an operating part 720, and a rotational shaft 730. When a pin inserted from the outside through the hole 165 presses the pressing unit 715, the pressing unit 715 may transfer force to a first end portion 720a of the operating part 720. The operating part 720 may rotate about the rotational shaft 730 by the force applied to the first end portion 720a of the operating part 720. A second end portion 720b of the operating part 720 may push the tray 160 toward the outside as the operating part 720 rotates.

The connector 210 may include a seal 710 interposed between the first passage 651 and the pressing unit 715. The seal 710 may allow air, which is introduced through the hole 165 and the first passage 651, to be introduced into the gas sensor 315 along the second passage 652. In addition, the seal 710 may block air, which is produced inside the electronic device 101, from being introduced into the gas sensor 315 along the second passage 652. The seal 710 may be implemented by using an elastic member (e.g., rubber).

Figure 8:
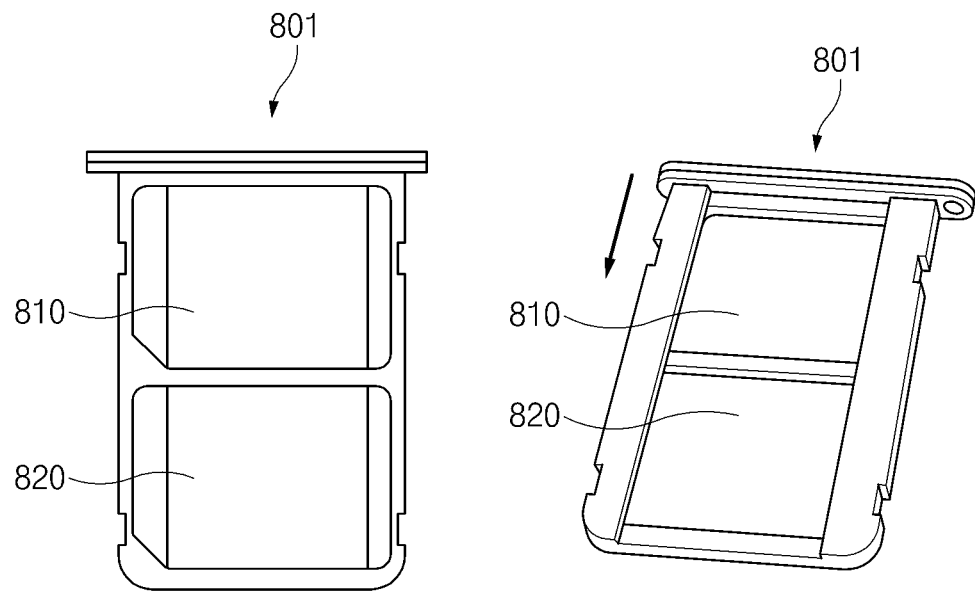
FIG. 8 is a diagram of a tray having a plurality of seating regions, according to an embodiment.

FIG. 8 is a diagram of the tray having a plurality of seating regions, according to an embodiment.

Referring to FIG. 8, a tray 801 includes a first seating region 810 and a second seating region 820. Although FIG. 8 illustrates that the first seating region 810 and the second seating region 820 having the same shape, the present disclosure is not limited thereto.

In the tray 801, two sensor modules, which are mutually different from each other, may be seated in the first seating region 810 and the second seating region 820. For example, a sensor module to detect CO or $CO_2$ may be seated in the first seating region 810 and a sensor module to detect the TVOC may be seated in the second seating region 820.

In the tray 801, one sensor module and a card other than the sensor module may be seated in the first seating region 810 and the second seating region 820, respectively. The sensor module to detect CO or $CO_2$ may be seated in the first seating region 810 and one of a USIM card or a memory card may be seated in the second seating region 820.

Figure 9:
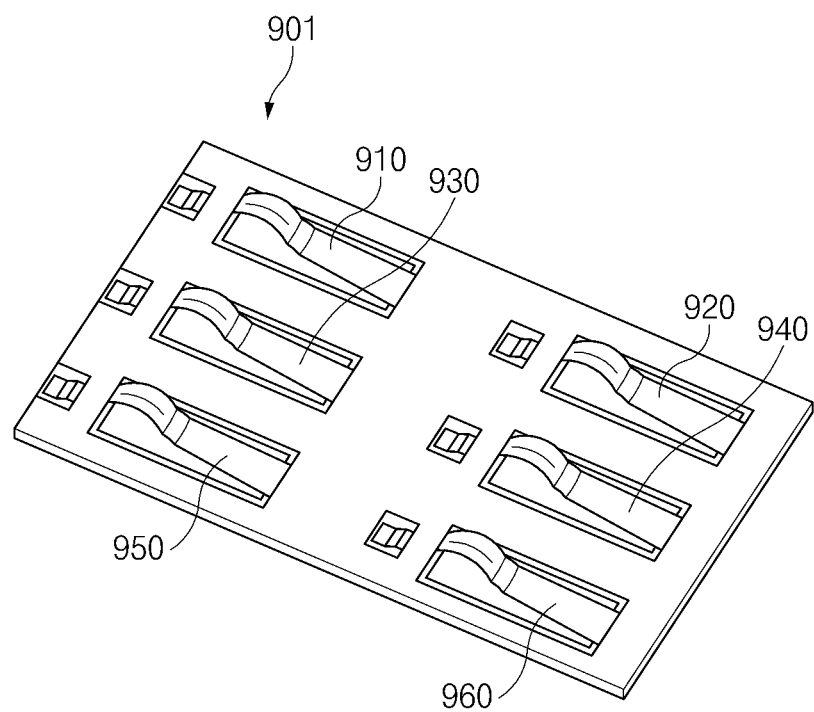
FIG. 9 is a diagram of pins of the connector, according to an embodiment.

FIG. 9 is a diagram of pins of the connector, according to an embodiment.

Referring to FIG. 9, the connector may include a plurality of pins provided at a sensor reader part (or the contact region) 901 of the connector. Although FIG. 9 illustrates that first to sixth pins 910 to 960 are included in the contact region 901 of the connector by way of example, the present disclosure is not limited thereto.

At least some of the first to six pins 910 to 960 (pogo pins) may be connected with respective terminals of the sensor module when the sensor module is inserted into the electronic device 101. The first pin 910 may be connected with the data terminal of the sensor module. The first pin 910 may transmit the collected gas information to the internal processor of the electronic device 101. The second pin 920 may be connected with the grounding. The fourth pin 940 may be connected with the power source.

Some of the first to sixth pins 910 to 960 may be activated and other of the first to sixth pins 910 to 960 may be deactivated, depending on the type of a card mounted on the tray. When the USIM card is seated on the tray and inserted, all the first to sixth pins 910 to 960 may be activated. When the sensor module is seated on the tray and inserted, three pins corresponding to the data terminal, the power terminal, and the grounding terminal of the sensor module may be activated and other pins may be deactivated.

Figure 10:
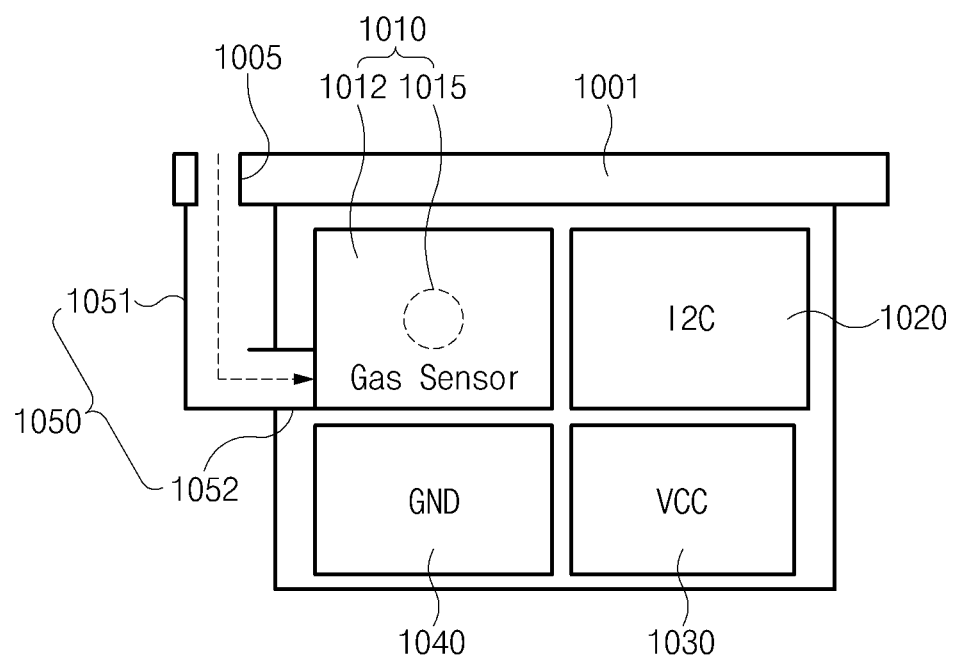
FIG. 10 is a diagram of the assembling structure of the tray and the sensor module, according to an embodiment.

FIG. 10 is a diagram of the structure that the tray and the sensor module are integrated with each other, according to an embodiment.

Referring to FIG. 10, a tray 1001 may be integrated with a sensor to sense the component of air which is present around a hole 1005. The tray 1001 includes the hole 1005, a gas sensor unit 1010, a data terminal 1020, a power terminal 1030, a grounding terminal 1040, and a pipe 1050. The operations of the gas sensor unit 1010, the data terminal 1020, the power terminal 1030, and the grounding terminal 1040 may be the same as or similar to the operations of corresponding components of FIG. 3.

The pipe 1050 may deliver air, which is introduced through the hole 1005, to the gas sensor unit 1010. The pipe 1050 may include a first passage 1051 and a second passage 1052. The first passage 1051 may extend from the hole 1005 in the direction that the tray 1001 is inserted into the electronic device. The second passage 1052 may connect the first passage 1051 with a sensor chamber 1012. The first passage 1051 and the second passage 1052 may be disposed perpendicular to each other.

A gas sensor 1015 may detect components of gas introduced through the hole 1005, the first passage 1051, and the second passage 1052 and may convert the detect result into an electrical signal.

Figure 11:
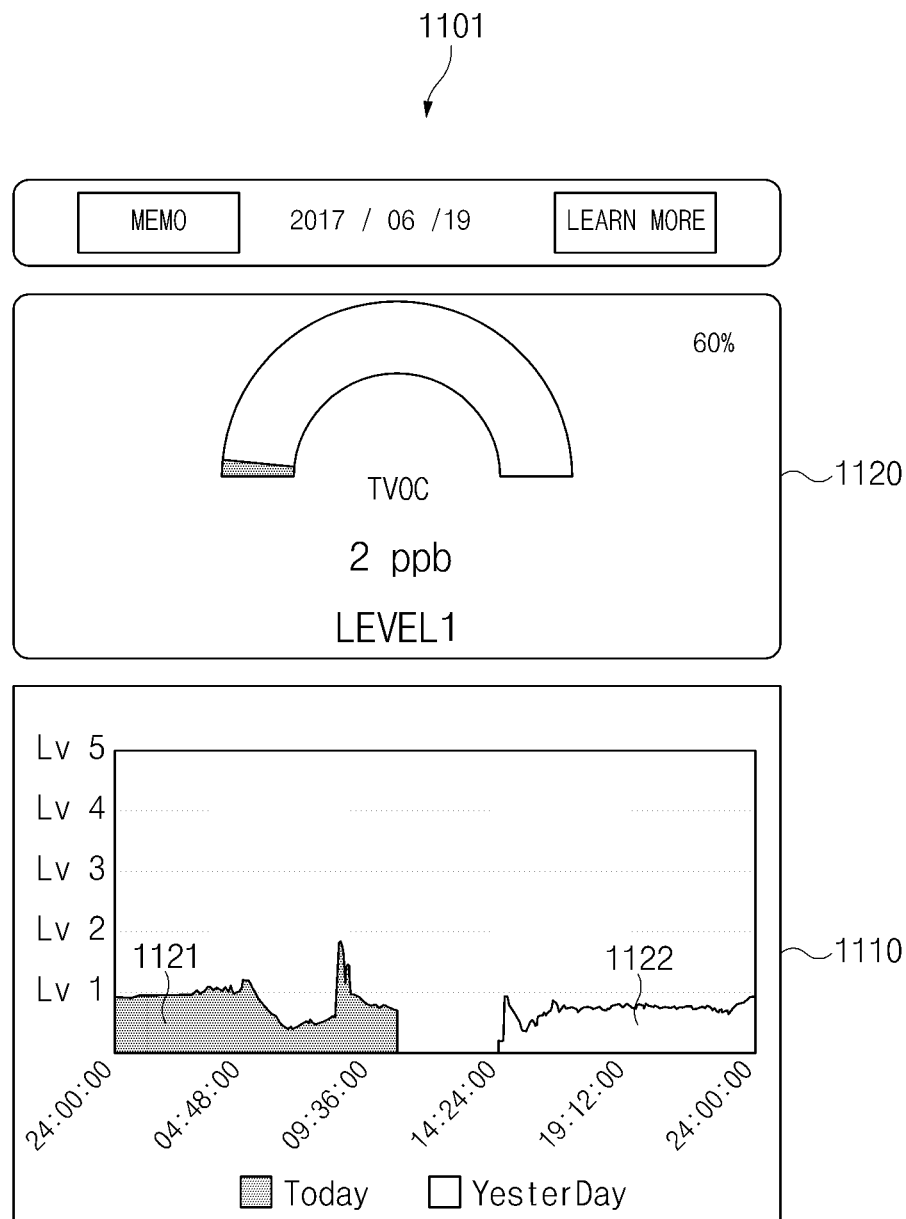
FIG. 11 is a diagram of a screen based on the sensing information, according to an embodiment.

FIG. 11 is a diagram of a screen based on the sensing information, according to an embodiment.

Referring to FIG. 11, a processor may output a user interface 1101 of an application, based on gas information collected by the sensor module.

The user interface 1101 may include a data region 1110 showing detected components of gas and an analysis region 1120 showing analysis information.

The data region 1110 may show the types and the ratios of the detected components. The data region 1110 may show component information 1121, which is measured today, and component information 1122 which is measured yesterday.

The analysis region 1120 may show information obtained by totally analyzing the collected gas information to provide, for a user, useful information. For example, the analysis region 1120 may show measured gas information (e.g., the index of bad breath) in the form of a numeric value (e.g., a part per billion (ppb) numeric value) or a graph. The analysis region 1120 may show information (e.g., please, often brush your teeth) for being recommended (suggested) to a user or may display a relevant alarm (e.g., "Toxic gas is spread out, so move fast"; alert).

The processor may record information on a region in which gas is detected, based on global positioning satellite (GPS) information and may provide the related service to the user.

A gas sensor containing a chemical specimen may provide information on various types of sensors for CO, $CO_2$, $C_2H_5OH$, or $CH_2O$, in addition to TVOC. In addition, another screen and another notification may be provided depending on a gas type. In addition, gas, which is difficult to be detected by a conventional electrical sensor, may be detected by using various chemical sensors. The gas sensor containing the chemical specimen may be periodically replaced. When the performance of the chemical specimen contained in the gas sensor is degraded, the user may purchase a new sensor, replace an old sensor with the new sensor, and use the new sensor.

Figure 12:
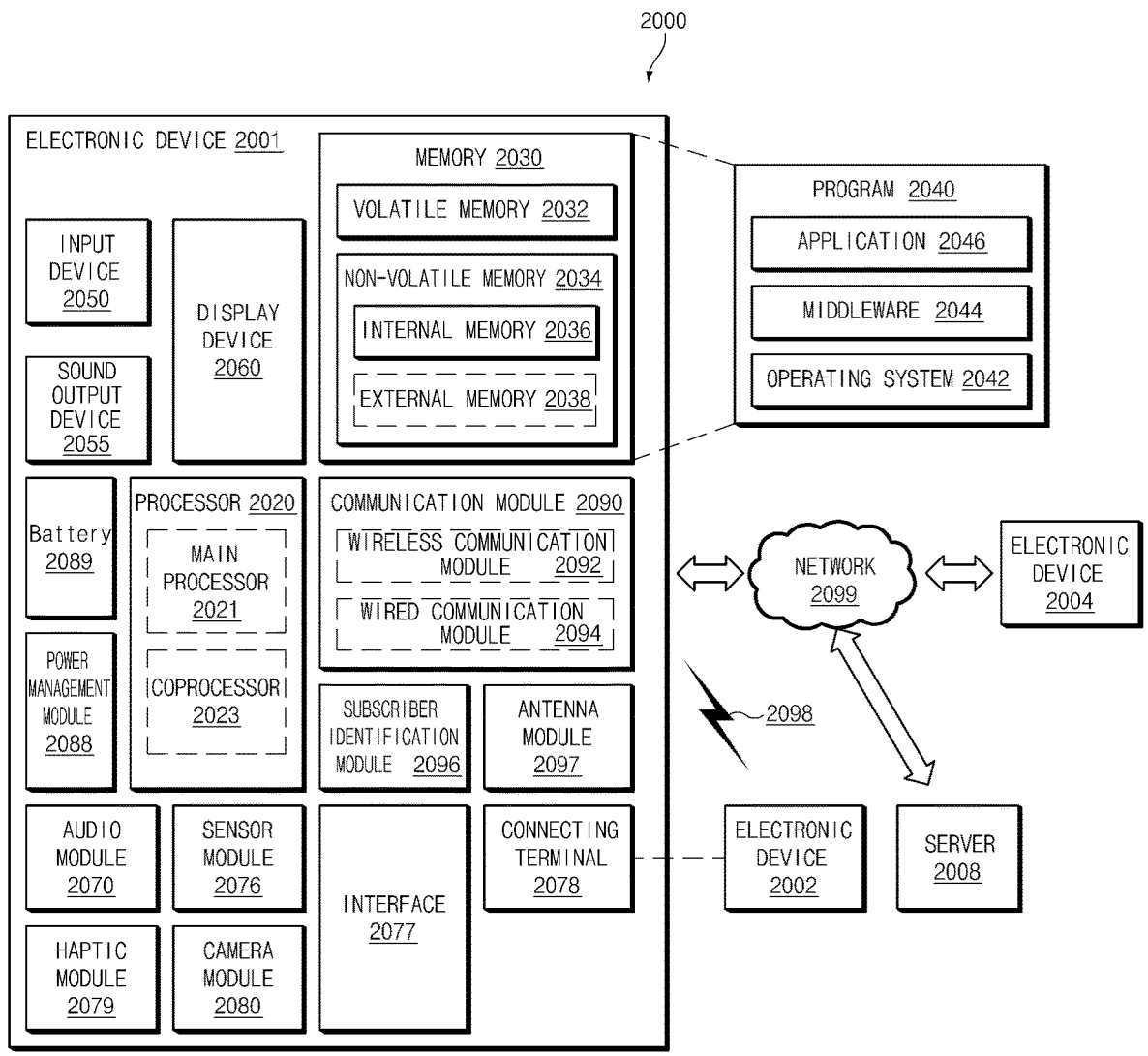
FIG. 12 is a diagram of an electronic device in a network environment, according to an embodiment.

FIG. 12 is a block diagram of an electronic device 2001 in a network environment 2000, according to various embodiments.

Referring to FIG. 12, the electronic device 2001 in the network environment 2000 may communicate with an electronic device 2002 over a first network 2098 (e.g., a short range wireless communication network) or may communicate with an electronic device 2004 or a server 2008 over a second network 2099 (e.g., a long distance wireless communication network). According to an embodiment, the electronic device 2001 may communicate with the electronic device 2004 through the server 2008. According to an embodiment, the electronic device 2001 may include a processor 2020, a memory 2030, an input device 2050, a sound output device 2055, a display device 2060, an audio module 2070, a sensor module 2076, an interface 2077, a haptic module 2079, a camera module 2080, a power management module 2088, a battery 2089, a communication module 2090, a subscriber identification module 2096, or an antenna module 2097. In any embodiment, at least one (e.g., the display device 2060 or the camera module 2080) of the components may be omitted from the electronic device 2001, or one or more other components may be further included in the electronic device 2001. In any embodiment, some of the components may be implemented with a single integrated circuit. For example, the sensor module 2076 (e.g., a fingerprint sensor, an iris sensor, or an illumination sensor) may be embedded in the display device 2060 (e.g., a display).

The processor 2020 may execute, for example, software (e.g., a program 2040) to control at least one other component (e.g., a hardware or software component) of the electronic device 2001 connected to the processor 2020, and may perform various data processing or operations. According to an embodiment, as at least a part of the data processing or operations, the processor 2020 may load a command or data received from any other component (e.g., the sensor module 2076 or the communication module 2090) to a volatile memory 2032, may process the command or data stored in the volatile memory 2032, and may store processed data in a nonvolatile memory 2034. According to an embodiment, the processor 2020 may include a main processor 2021 (e.g., a central processing unit or an application processor) and a coprocessor 2023 (e.g., a graphic processing device, an image signal processor, a sensor hub processor, or a communication processor), which may be operated independently of or together with the main processor 2021. Additionally or alternatively, the coprocessor 2023 may be configured to use lower power than the main processor 2021 or to be specialized for a specified function. The coprocessor 2023 may be implemented separately from the main processor 2021 or may be implemented as a part of the main processor 2021.

The coprocessor 2023 may control at least a part of a function or states associated with at least one component (e.g., the display device 2060, the sensor module 2076, or the communication module 2090) of the electronic device 2001, for example, instead of the main processor 2021 while the main processor 2021 is in an inactive (e.g., sleep) state and together with the main processor 2021 while the main processor 2021 is in an active (e.g., an application execution) state. According to an embodiment, the coprocessor 2023 (e.g., an image signal processor or a communication processor) may be implemented as a part of any other component (e.g., the camera module 2080 or the communication module 2090) which is functionally (or operatively) associated with the coprocessor 2023.

The memory 2030 may store various data which are used by at least one component (e.g., the processor 2020 or the sensor module 2076) of the electronic device 2001. The data may include, for example, software (e.g., the program 2040), or input data or output data associated with a command of the software. The memory 2030 may include the volatile memory 2032 or the nonvolatile memory 2034. The nonvolatile memory 2034 may include an internal memory 2036 and an external memory 2038.

The program 2040 may be stored in the memory 2030 as software, and may include, for example, an operating system 2042, a middleware 2044, or an application 2046.

The input device 2050 may receive a commands or data which will be used by a component (e.g., the processor 2020) of the electronic device 2001, from the outside (e.g., a user) of the electronic device 2001. The input device 2050 may include, for example, a microphone, a mouse, or a keyboard.

The sound output device 2055 may output a sound signal to the outside of the electronic device 2001. The sound output device 2055 may include, for example, a speaker or a receiver. The speaker may be used for a general purpose such as multimedia play or recording play, and the receiver may be used to receive an incoming call. According to an embodiment, the receiver may be implemented separately from the speaker or may be implemented as a part of the speaker.

The display device 2060 may visually provide information to the outside (e.g., the user) of the electronic device 2001. The display device 2060 may include, for example, a display, a hologram device, or a control circuit for controlling a projector and a corresponding device. According to an embodiment, the display device 2060 may include a touch circuitry configured to sense a touch, or a sensor circuitry (e.g., a pressure sensor) configured to measure the strength of force generated by the touch.

The audio module 2070 may convert sound to an electrical signal, or reversely, may convert an electrical signal to sound. According to an embodiment, the audio module 2070 may obtain sound through the input device 2050, or may output sound through the sound output device 2055, or through an external electronic device (e.g., the electronic device 2002) (e.g., a speaker or a headphone) directly or wirelessly connected with the electronic device 2001.

The sensor module 2076 may sense an operation state (e.g., power or a temperature) of the electronic device 2001 or an external environment state (e.g., a user state), and may generate an electrical signal or a data value corresponding the sensed state. According to an embodiment, the sensor module 2076 may include, for example, a gesture sensor, a grip sensor, a barometric pressure sensor, a magnetic sensor, an acceleration sensor, a grip sensor, a proximity sensor, a color sensor, an infrared (IR) sensor, a biometric sensor, a temperature sensor, a humidity sensor, or an illumination sensor.

The interface 2077 may support one or more specified protocols that may be used to directly and wirelessly connect the electronic device 2001 with an external electronic device (e.g., the electronic device 2002). According to an embodiment, the interface 2077 may include, for example, a high definition multimedia interface (HDMI), a universal serial bus (USB) interface, a secure digital (SD) card interface, or an audio interface.

A connection terminal 2078 may include a connector that may allow the electronic device 2001 to be physically connected with an external electronic device (e.g., the electronic device 2002). According to an embodiment, the connection terminal 2078 may include, for example, a HDMI connector, a USB connector, a SD card connector, or an audio connector (e.g., a headphone connector).

The haptic module 2079 may convert an electrical signal to a mechanical stimulation (e.g., vibration or movement) or an electrical stimulation which the user may perceive through the sense of touch or the sense of movement. According to an embodiment, the haptic module 2079 may include, for example, a motor, a piezoelectric sensor, or an electrical stimulation device.

The camera module 2080 may photograph a still image and a video. According to an embodiment, the camera module 2080 may include one or more lenses, image sensors, image signal processors, or flashes (or electrical flashes).

The power management module 2088 may manage the power which is supplied to the electronic device 2001. According to an embodiment, the power management module 2088 may be implemented, for example, as at least a part of a power management integrated circuit (PMIC).

The battery 2089 may power at least one component of the electronic device 2001. According to an embodiment, the battery 2089 may include, for example, a primary cell not recharged, a secondary cell rechargeable, or a fuel cell.

The communication module 2090 may establish a direct (or wired) communication channel or a wireless communication channel between the electronic device 2001 and an external electronic device (e.g., the electronic device 2002, the electronic device 2004, or the server 2008) or may perform communication through the established communication channel. The communication module 2090 may include one or more communication processors which is operated independently of the processor 2020 (e.g., an application processor) and supports direct (or wired) communication or wireless communication. According to an embodiment, the communication module 2090 may include a wireless communication module 2092 (e.g., a cellular communication module, a short range wireless communication module, or a global navigation satellite system (GNSS) communication module) or a wired communication module 2094 (e.g., a local area network (LAN) communication module or a power line communication module). A corresponding communication module of such communication modules may communicate with an external electronic device over the first network 2098 (e.g., a short range communication network such as Bluetooth, Wi-Fi direct, or infrared data association (IrDA)) or the second network 2099 (e.g., a long distance communication network such as a cellular network, an Internet, or a computer network (e.g., LAN or WAN)). The above-described kinds of communication modules may be integrated in one component (e.g., a single chip) or may be implemented with a plurality of components (e.g., a plurality of chips) which are independent of each other. The wireless communication module 2092 may verify and authenticate the electronic device 2001 within a communication network, such as the first network 2098 or the second network 2099, by using subscriber information (e.g., international mobile subscriber identity (IMSI)) stored in the subscriber identification module 2096.

The antenna module 2097 may transmit a signal or a power to the outside (e.g., an external electronic device) or may receive a signal or a power from the outside. According to an embodiment, the antenna module 2097 may include one or more antennas, and at least one antenna which is suitable for a communication scheme used in a computer network such as the first network 2098 or the second network 2099 may be selected, for example, by the communication module 2090 from the one or more antennas. The signal or power may be exchanged between the communication module 2090 and an external electronic device through the selected at least one antenna or may be received from the external electronic device through the selected at least one antenna and the communication module 2090.

At least some of the components may be connected to each other through a communication scheme (e.g., a bus, a general purpose input and output (GPIO), a serial peripheral interface (SPI), or a mobile industry processor interface (MIPI)) between peripheral devices and may exchange signals (e.g., commands or data) with each other.

According to an embodiment, a command or data may be transmitted or received (or exchanged) between the electronic device 2001 and the external electronic device 2004 through the server 2008 connecting to the second network 2099. Each of the electronic devices 2002 and 2004 may be a device, the kind of which is the same as or different from a kind of the electronic device 2001. According to an embodiment, all or a part of operations to be executed in the electronic device 2001 may be executed in one or more external devices of the external electronic devices 2002, 2004, or server 2008. For example, in the case where the electronic device 2001 should perform any function or service automatically or in response to a request from the user or any other device, the electronic device 2001 may request one or more external electronic devices to perform at least a part of the function or service, instead of internally executing the function or service or additionally. The one or more external electronic devices which receive the request may execute at least a part of the function or service thus requested or an additional function or service associated with the request, and may provide a result of the execution to the electronic device 2001. The electronic device 2001 may process received result as it is or additionally, and may provide a result of the processing as at least a part of the response to the request. To this end, for example, a cloud computing, distributed computing, or client-server computing technology may be used.

According to various embodiments, an electronic device includes a display disposed toward a first surface, a housing including an opening formed toward a second surface, a tray including a hole formed toward the second surface, a sensor module that is able to be seated on the tray, a connector disposed adjacent to the opening inside the electronic device to receive the tray and the sensor module, and a processor configured to control the sensor module when the sensor module is inserted into the connector, wherein the sensor module includes a gas sensor, a sensor chamber, and a pipe forming a path allowing gas, which is introduced through the hole, to move into the sensor chamber.

According to various embodiments, the gas sensor detects a component of the gas introduced through the hole and the pipe. The gas sensor detects the component of the introduced gas by using a chemical specimen.

According to various embodiments, the sensor module includes a data terminal, a power terminal, and a grounding terminal, and the data terminal transmits a detection result, which is obtained through the gas sensor, to the processor. The data terminal transmits the detection result to the processor through inter-integrated communication (I2C).

According to various embodiments, the sensor chamber surrounds the gas sensor; and spatially separates an inner region of the electronic device from the gas sensor.

According to various embodiments, the sensor chamber blocks gas, which is produced inside the electronic device, from being introduced into the gas sensor.

According to various embodiments, the sensor module includes a membrane which blocks a foreign matter from moving into the sensor chamber, inside the pipe.

According to various embodiments, the sensor module has an external shape the same as an external shape of a universal subscriber identity module (USIM).

According to various embodiments, the tray includes a first seating region and a second seating region, wherein the sensor module is seated in the first seating region, and wherein one of a USIM card or a memory card is seated in the second seating region.

According to various embodiments, the connector includes a first passage extending from the hole in a first direction of facing an inner part of the electronic device, and a second passage formed to have a specified angle with respect to the first direction. The second passage spatially connects the first passage with the pipe. The second passage is formed perpendicularly to the first passage. The connector includes a seal at an end portion of the first passage, which is opposite to the hole. The seal is formed of an elastic member. The connector includes a withdrawing structure to withdraw the tray, and a portion of the withdrawing structure makes contact with the seal in a direction opposite to a direction of the first passage.

According to various embodiments, the connector includes a plurality of pins, and wherein at least some of the plurality of pins are electrically connected with a data terminal, a power terminal, and a grounding terminal of the sensor module.

According to various embodiments, the processor is configured to output a user interface to the display, based on information detected by the gas sensor. The processor is configured to display information on a component of detected gas and information to be recommended to a user based on the component information, through the user interface. The processor is configured to collect information on a state of the sensor module and display, through the user interface, information on whether the sensor module is replaced based on the state information. The processor is configured to store, in a memory, information on gas detected by the sensor module based on location information of the electronic device.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device, comprising:
   a display disposed toward a first surface;
   a housing including an opening formed toward a second surface;
   a tray including a hole formed toward the second surface;
   a sensor module that is able to be seated on the tray;
   a processor configured to control the sensor module when the sensor module is inserted into the connector,
   wherein the sensor module includes a gas sensor, a sensor chamber, and a pipe forming a path allowing gas, which is introduced through the hole, to move into the sensor chamber; and
   a connector disposed adjacent to the opening inside the electronic device to receive the tray and the sensor module, wherein the connector includes:
      a first passage extending from the hole in a first direction facing an inner part of the electronic device; and
      a second passage formed to have a specified angle with respect to the first direction, and
      wherein the second passage spatially connects the first passage with the pipe.

2. The electronic device of claim 1, wherein the gas sensor detects a component of the gas introduced through the hole and the pipe.

3. The electronic device of claim 2, wherein the gas sensor detects the component of the introduced gas by using a chemical specimen.

4. The electronic device of claim 1, wherein the sensor module further includes a data terminal, a power terminal, and a grounding terminal, and
   wherein the data terminal transmits a detection result, which is obtained through the gas sensor, to the processor.

5. The electronic device of claim 4, wherein the data terminal transmits the detection result to the processor through inter-integrated communication.

6. The electronic device of claim 1, wherein the sensor chamber:
   surrounds the gas sensor; and
   spatially separates an inner region of the electronic device from the gas sensor.

7. The electronic device of claim 1, wherein the sensor chamber blocks gas, which is produced inside the electronic device, from being introduced into the gas sensor.

8. The electronic device of claim 1, wherein the sensor module further includes a membrane inside the pipe which blocks foreign matter from moving into the sensor chamber.

9. The electronic device of claim 1, wherein the sensor module has an external shape corresponding to an external shape of a universal subscriber identity module.

10. The electronic device of claim 1, wherein the tray includes:
    a first seating region and a second seating region,
    wherein the sensor module is seated in the first seating region, and
    wherein one of a universal subscriber identity module card or a memory card is seated in the second seating region.

11. The electronic device of claim 1, wherein the second passage is formed perpendicular to the first passage.

12. The electronic device of claim 1, wherein the connector includes a seal at an end portion of the first passage, which is opposite to the hole.

13. The electronic device of claim 12, wherein the seal is formed of an elastic member.

14. The electronic device of claim 12, wherein the connector further includes:
    a withdrawing structure to withdraw the tray, and
    wherein a portion of the withdrawing structure makes contact with the seal in a direction opposite to the first direction.

15. The electronic device of claim 1, wherein the connector includes:
    a plurality of pins, and
    wherein at least some of the plurality of pins are electrically connected with a data terminal, a power terminal, and a grounding terminal of the sensor module.

16. The electronic device of claim 1, wherein the processor is further configured to:
    output a user interface to the display, based on information detected by the gas sensor.

17. The electronic device of claim 16, wherein the processor is further configured to:

display information on a component of detected gas and information to be recommended to a user based on the component information, through the user interface.

18. The electronic device of claim 16, wherein the processor is further configured to:
collect information on a state of the sensor module and display, through the user interface, information on whether the sensor module is replaced based on the state information.

19. The electronic device of claim 16, wherein the processor is further configured to:
store, in a memory, information on gas detected by the sensor module based on location information of the electronic device.

* * * * *